(12) United States Patent
Wada et al.

(10) Patent No.: US 10,137,119 B2
(45) Date of Patent: Nov. 27, 2018

(54) ANTI-MALARIAL AGENT

(71) Applicant: RIKEN, Wako-shi, Saitama (JP)

(72) Inventors: Akira Wada, Wako (JP); Hiroki Hayase, Wako (JP); Nobumoto Watanabe, Wako (JP); Hiroyuki Osada, Wako (JP); Takeshi Shimizu, Wako (JP); Konstanty Wierzba, Wako (JP)

(73) Assignee: RIKEN, Wako (JP)

( * ) Notice: Subject to any disclaimer, the term of this patent is extended or adjusted under 35 U.S.C. 154(b) by 0 days.

(21) Appl. No.: 15/847,432

(22) Filed: Dec. 19, 2017

(65) Prior Publication Data

US 2018/0104226 A1    Apr. 19, 2018

Related U.S. Application Data

(63) Continuation-in-part of application No. 15/110,708, filed as application No. PCT/JP2015/050513 on Jan. 9, 2015, now Pat. No. 9,861,626.

(30) Foreign Application Priority Data

Jan. 9, 2014    (JP) .................. 2014-002428

(51) Int. Cl.
*A61K 31/444*    (2006.01)
*A61K 31/315*    (2006.01)
(Continued)

(52) U.S. Cl.
CPC .......... *A61K 31/444* (2013.01); *A61K 31/315* (2013.01); *A61K 31/4745* (2013.01); *A61P 33/06* (2018.01)

(58) Field of Classification Search
CPC ................ A61K 31/444; A61K 31/315; A61K 31/4745; A61P 33/06
(Continued)

(56) References Cited

U.S. PATENT DOCUMENTS 8,507,546 B2 *    8/2013    Hannus ................ A61K 31/122
                                                              514/430
2002/0013306 A1    1/2002    Lowe
2013/0096090 A1    4/2013    Merola

FOREIGN PATENT DOCUMENTS

JP    2000-503982 A    4/2000

OTHER PUBLICATIONS

Walcourt et al. The international Journal of Biochemistry & Cell Biology, 2004, 36, 401-407.*

(Continued)

*Primary Examiner* — Yevgeny Valenrod
(74) *Attorney, Agent, or Firm* — Leydig, Voit & Mayer, Ltd.

(57) ABSTRACT

The invention aims to prevent and/or treat malaria using an antimalarial drug comprising, as an active ingredient, a metal chelator represented by the following formula (I), (III), (IV), (V), (VI), or (VII), such as tris(2-pyridylmethyl) amine.

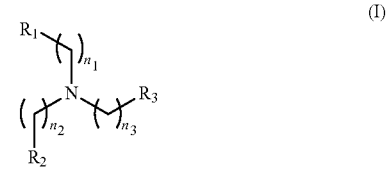

(I)

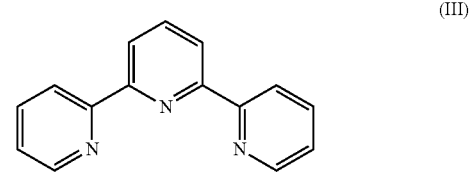

(III)

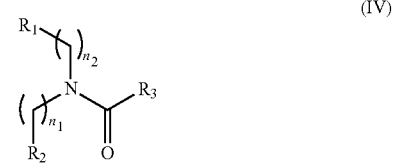

(IV)

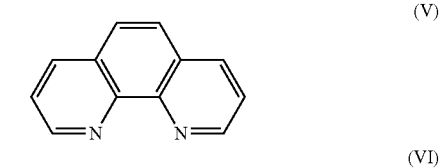

(V)

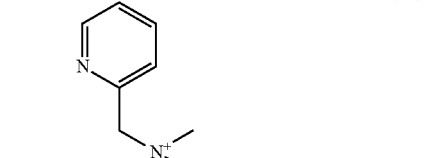

(VI)

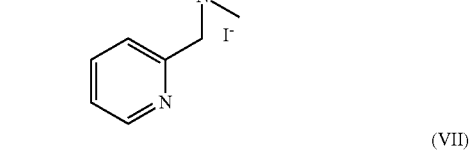

(VII)

8 Claims, 4 Drawing Sheets

(51) Int. Cl.
*A61K 31/4745* (2006.01)
*A61P 33/06* (2006.01)
(58) Field of Classification Search
USPC .......................................................... 514/64
See application file for complete search history.

(56) References Cited

OTHER PUBLICATIONS

Rupp et al Molecular & Biochemical Parasitology, 2008, 158, 208-212.*
Egan et al., *Journal of Medicinal Chemistry*, 47(11): 2926-2934 (2004).
Ginsburg et al., *Biochimica et Biophysica Acta*, 886: 337-344 (1986).
Glickstein et al., *Blood*, 87(11): 4871-4878 (1996).
Huang et al., *Metallomics*, 5(6): 648-655 (2013).
Kitjaroentham et al., *Acta Tropica*, 97(1): 5-9 (2006).
Kuter et al., *Journal of Inorganic Biochemistry*, 105: 684-692 (2011).
Labadie et al., *Bioorg. Med. Chem. Lett.*, 14(3): 615-619 (2004).
Labadie et al., *Med. Chem. Res.*, 14(6): 332-346 (2005).
Marvin et al., *Chemistry and Biology*, 19(6): 731-741 (2012).
Pradines et al., *Antimicrob. Agents Chemother.*, 40(9): 2094-2098 (1996).
Quirante et al., *J. Inorg. Biochem.*, 105(12): 1720-1728 (2011).
Rasoloson et al., *The Biochem. Journal*, 381: 803-811 (2004).
Sall et al., *Bioorganic & Medicinal Chemistry Letters*, 18(16): 4666-4669 (2008).
Yapi et al., *Arch. Pharm. Chem. Life Sci.*, 339(4): 201-206 (2006).
Yapi et al., *Chem. Pharm. Bull.*, 48(12): 1886-1889 (2000).
European Patent Office, Supplementary Partial European Search Report in European Patent Application No. 15735415.0 (dated Sep. 8, 2017).
Japanese Patent Office, International Search Report in International Patent Application No. PCT/JP2015/050513 (dated Mar. 31, 2015).
International Bureau of WIPO, International Preliminary Report on Patentability in International Patent Application No. PCT/JP2015/050513 (dated Jul. 21, 2016).
U.S. Appl. No. 15/110,708, filed Jul. 8, 2016.

* cited by examiner

ANTI-MALARIAL AGENT

CROSS-REFERENCE TO RELATED APPLICATIONS

This patent application is continuation-in-part of copending U.S. patent application Ser. No. 15/110,708, filed on Jul. 8, 2016, which is the U.S. national phase of International Patent Application No. PCT/JP2015/050513, filed Jan. 9, 2015, which claims the benefit of Japanese Patent Application No. 2014-002428, filed on Jan. 9, 2014, which are incorporated by reference in their entireties herein.

TECHNICAL FIELD

The present invention relates to an antimalarial drug.

BACKGROUND ART

Malaria is a protozoan infection whose pathogen is a malaria parasite. Infection with malaria has been found in not less than 100 countries in the world. According to estimation by the World Health Organization (WHO), about 500 million people are infected with malaria per year, and about 1.5 million people die of malaria every year. For treatment of malaria, drugs such as artemisinin, chloroquine, and atovaquone have been used. However, the number of types of the drugs is small compared to drugs for other infections. Moreover, in view of the current situation where malaria parasites resistant to the drugs described above are found, it is clear that development of novel therapeutic and prophylactic agents for malaria is an urgent task.

Invasion of malaria parasites into the body is mediated by anopheline mosquitoes. After infection of erythrocytes with the malaria parasites, the malaria parasites grow by degradation and utilization of proteins and lipids in the erythrocytes. When the nutrient becomes insufficient, the malaria parasites destroy the cell membrane, and cause infection of other erythrocytes. Therefore, natural compounds and synthetic compounds that are capable of specifically inhibiting this life cycle may be hopeful as novel antimalarial drugs. Artemisinin is activated by iron ion, and inhibits the function of an endoplasmic reticulum-type calcium pump, PfATP6, to exhibit the antimalarial activity. Chloroquine exhibits its antimalarial activity by inhibition of the detoxification process in which ferriprotoporphyrin IX is polymerized to produce hemozoin. Atovaquone specifically inhibits the electron transfer system driven by cytochrome bc1, to exhibit the antimalarial activity.

In recent years, "metallomics", which is research for elucidation of roles and significances of trace metal elements (zinc, iron, copper, and the like) that are involved in life phenomena and cellular functions, is attracting attention. In particular, it has been suggested not only that zinc ion is deeply involved in maintenance of the structures of proteins, activation of metalloenzymes, nucleic acid synthesis, transcription regulation, second messengers, and the like, but also that it influences cell death, oxidative stress, carcinogenesis, and the like. In terms of association with malaria, it has been reported that, in the growth cycle of malaria parasites, the zinc ion concentration in the erythrocytes infected with malaria parasites increases in accordance with an increase in the DNA concentration (Non-patent Document 1). It has also been reported that N,N,N',N'-tetrakis(2-pyridylmethyl)ethylenediamine (TPEN), which is a zinc chelator, inhibits infection with malaria parasites (Non-patent Document 1).

As metal chelators having antimalarial activity, dipicolinic acid (DPA, Non-patent Document 2) and desferrioxamine (DFO; Non-patent Document 3) have been reported. However, neither of these exhibits high antimalarial activity (DPA, antimalarial activity $ED_{50}=1$ mM; DFO, antimalarial activity $IC_{50}=21$ μM, cell growth inhibition $IC_{50}=7$ to 21 μM).

PRIOR ART DOCUMENTS

Non-Patent Documents

Non-patent Document 1: Marvin R G, et al., Chem Biol. 2012 Jun. 22; 19(6): 731-41.
Non-patent Document 2: Ginsburg H, et al., Biochim Biophys Acta. 1986 May 29; 886(3): 337-44.
Non-patent Document 3: Glickstein H, et al., Blood. 1996 Jun. 1; 87(11): 4871-8.

SUMMARY OF THE INVENTION

Problems to be Solved by the Invention

An object of the present invention is to provide means for preventing and/or treating malaria.

Means for Solving the Problems

The present inventors intensive studied to solve the problems described above and, as a result, discovered that metal chelators such as tris(2-pyridylmethyl)amine have high antimalarial activity, thereby completed the present invention.

That is, the present invention provides the followings.

[1]
An antimalarial drug comprising, as an active ingredient(s), one or more compounds selected from the group consisting of compounds represented by the following Formula (I), compounds represented by the following Formula (III), compounds represented by the following Formula (IV), compounds represented by the following Formula (V), compounds represented by the following Formula (VI), and compounds represented by the following Formula (VII):

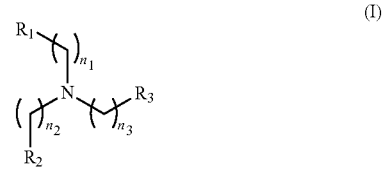

(in Formula (I), $R_1$, $R_2$, and $R_3$ each independently represent a group represented by the following Formula (II-1), (II-2), or (II-3), or hydrogen, $C_1$-$C_5$ alkyl, or phenyl; and, in Formula (I), $n_1$, $n_2$, and $n_3$ each independently represent 1 or 2);

(in Formula (II-1), any one of the Xs represents carbon (C) or nitrogen (N), and the other three Xs represent carbon (C));

(in Formula (II-2), each X independently represents carbon (C) or nitrogen (N), and Y represents carbon (C), nitrogen (N), or boron (B));

$$—NR_4R_5 \quad (II-3)$$

(in Formula (II-3), $R_4$ and $R_5$ each independently represent hydrogen or $C_1$-$C_5$ alkyl);

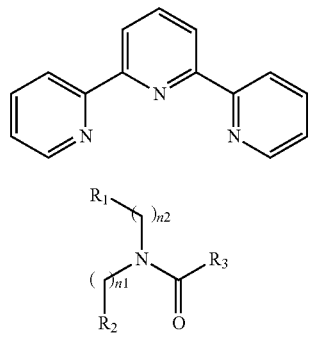

(III)

(IV)

(in Formula (IV), $R_1$, $R_2$, and $R_3$ each independently represent a group represented by the above Formula (II-1), Formula (II-2), or Formula (II-3), or hydrogen, $C_1$-$C_5$ alkyl, phenyl, or phenylmethoxy; and, in Formula (IV), $n_1$ and $n_2$ each independently represent 1 or 2);

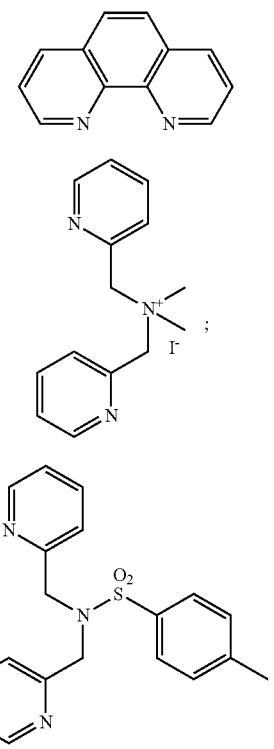

(V)

(VI)

(VII)

(in Formula (II-1), Formula (II-2), Formula (III), and Formula (V), each hydrogen (H) is optionally independently substituted with a halogen, $C_1$-$C_{10}$ alkyl, $C_1$-$C_{10}$ alkoxy, phenyl, hydroxyl (—OH), carboxyl (—COOH), amino (—NH$_2$), benzamide (—NHCOC$_6$H$_5$), benzylamino (—NHCH$_2$C$_6$H$_5$), tert-butylamide (—NHCO-tBu), neopentylamino (—NHCH$_2$-tBu), —C(=O)OR, —S(=O)$_2$OR, or —OP(=O)(OR)(OR'); R and R' each independently represent hydrogen or $C_1$-$C_{10}$ alkyl; and further, each hydrogen (H) in the alkyl, alkoxy, phenyl, "—C$_6$H$_5$" of the benzamide, "—C$_6$H$_5$" of the benzylamino, "-tBu" of the tert-butylamide, and "—CH$_2$—" and "-tBu" of the neopentylamino is optionally independently substituted with a halogen, hydroxyl, amino, —C(=O)OR, —S(=O)$_2$OR, or —OP(=O)(OR)(OR')); and pharmaceutically acceptable salts and metal complexes thereof.

[2]
The antimalarial drug according to [1], wherein, in the Formula (I), each of $n_1$, $n_2$, and $n_3$ is 1.

[3]
The antimalarial drug according to [1] or [2], wherein, in the Formula (I), each of $R_1$, $R_2$, and $R_3$ is a group represented by the Formula (II-1).

[4]
The antimalarial drug according to [1], wherein the compound represented by the Formula (I) is tris(2-pyridylmethyl)amine.

[5]
The antimalarial drug according to [1], wherein the compound represented by the Formula (III) is 2,2':6',2''-terpyridine.

[6]
The antimalarial drug according to [1], wherein the compound represented by the Formula (V) is either one of the following compounds:

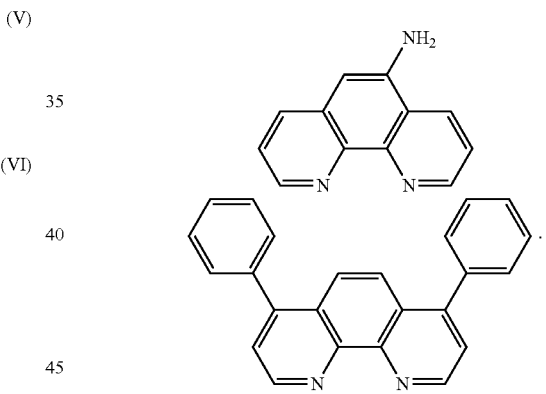

[7]
The antimalarial drug according to any one of [1] to [6], wherein the metal complex is a zinc complex.

[8]
A method of treating or preventing malaria, comprising administering a therapeutically or prophylactically effective amount(s) of one or more compounds selected from the group consisting of the compounds represented by the above Formula (I), the compounds represented by the above Formula (III), the compounds represented by the above Formula (IV), the compounds represented by the above Formula (V), the compounds represented by the above Formula (VI), and the compounds represented by the above Formula (VII), and pharmaceutically acceptable salts and metal complexes thereof, to a subject suffering from malaria or a subject suspected of having malaria.

[9]
A compound represented by the above Formula (I), a compound represented by the above Formula (III), a compound represented by the above Formula (IV), a compound represented by the above Formula (V), a compound represented by the above Formula (VI), or a compound represented by the above Formula (VII), or a pharmaceutically acceptable salt or metal complex thereof, for use in treatment and/or prevention of malaria.

EFFECT OF THE INVENTION

By the present invention, malaria can be effectively prevented and/or treated.

EMBODIMENTS FOR CARRYING OUT THE INVENTION

Figure 1:
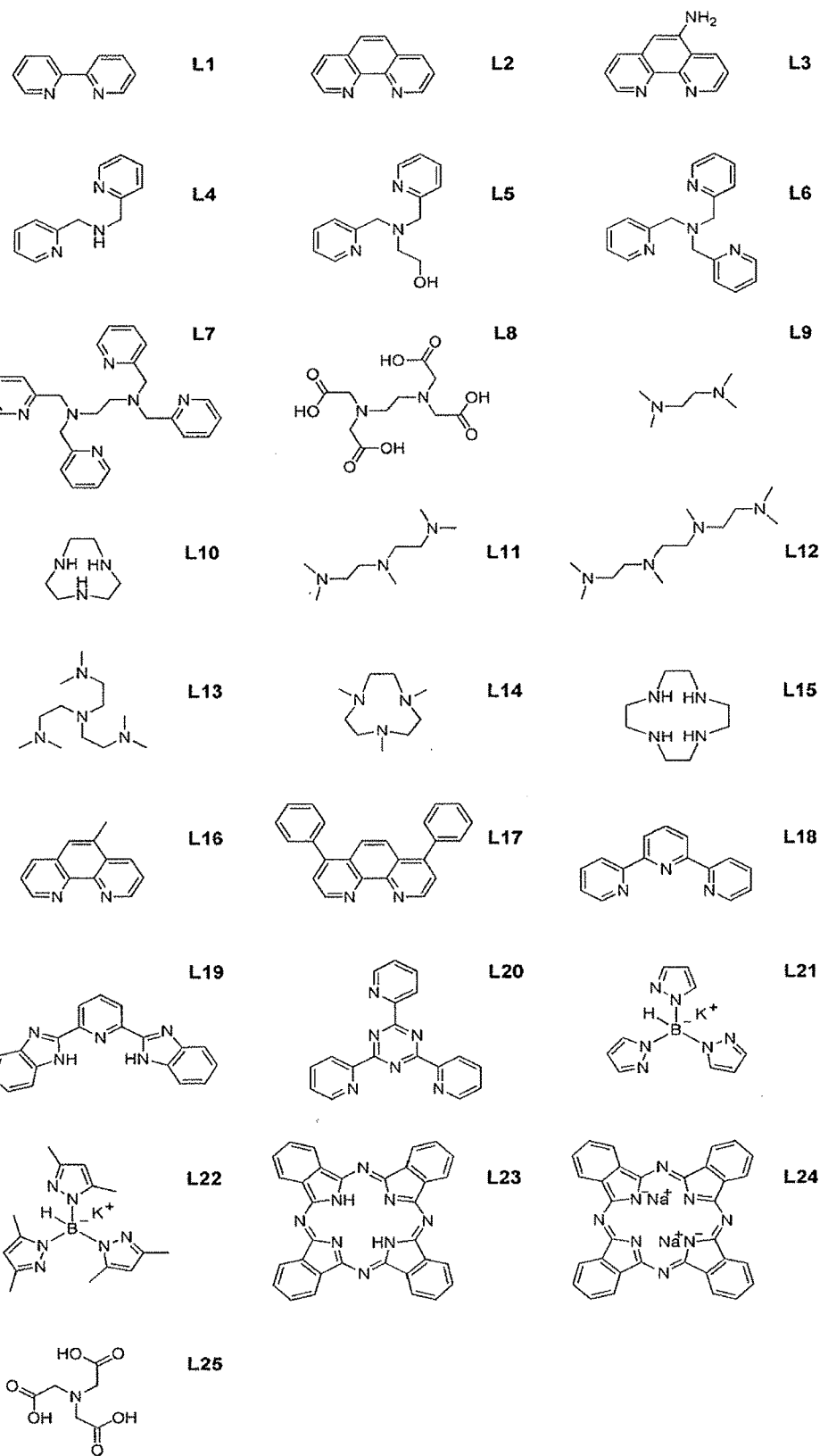
FIG. 1 is a diagram illustrating the structures of metal chelators.

The present invention is described below in detail.

The antimalarial drug of the present invention is an antimalarial drug comprising, as an active ingredient(s), one or more compounds selected from the group consisting of compounds represented by the Formula (I), compounds represented by the Formula (III), compounds represented by the Formula (IV), compounds represented by the Formula (V), compounds represented by the Formula (VI), compounds represented by the Formula (VII), and compounds represented by the Formula (VIII), and pharmaceutically acceptable salts and metal complexes thereof. In the present invention, the one or more compounds selected from the group consisting of compounds represented by the Formula (I), compounds represented by the Formula (III), compounds represented by the Formula (IV), compounds represented by the Formula (V), compounds represented by the Formula (VI), compounds represented by the Formula (VII), and compounds represented by the Formula (VIII), and pharmaceutically acceptable salts and metal complexes thereof, contained in the antimalarial drug of the present invention are also referred to as "active ingredients".

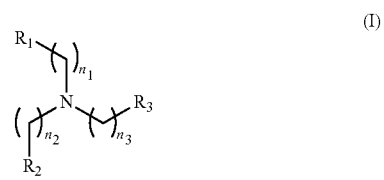

In Formula (I), $n_1$, $n_2$, and $n_3$ each independently represent 1 or 2. In Formula (I), $R_1$, $R_2$, and $R_3$ each independently represent a group represented by the Formula (II-1), (II-2), or (II-3), or hydrogen, $C_1$-$C_5$ alkyl, or phenyl. For simplicity of description, the group represented by the Formula (II-1) may be referred to as "pyridine-type substituent"; the group represented by the Formula (II-2) may be referred to as "imidazole-type substituent"; and the group represented by the Formula (II-3) may be referred to as "ethylamine-type substituent". All of $R_1$, $R_2$, and $R_3$ preferably represent a group(s) represented by the Formula (II-1).

In Formula (II-1), any one of the Xs represents carbon (C) or nitrogen (N), and the other three Xs represent carbon (C). Preferably, all of the Xs represent carbon (C). Each substituent represented by Formula (II-1) is bound as a substituent $R_1$, $R_2$, or $R_3$ through a carbon atom of the 6-membered ring.

Specific examples of the substituent represented by Formula (II-1) include those having the following structural formulae. In the following structural formulae, each hydrogen (H) may be independently substituted as described later.

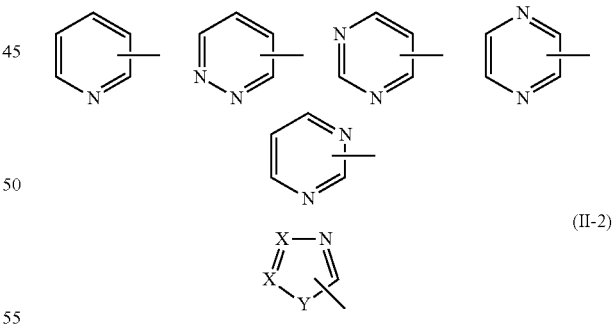

In Formula (II-2), each X independently represents carbon (C) or nitrogen (N), and Y represents carbon (C), nitrogen (N), or boron (B). Preferably, all of the Xs represent carbon (C). Each substituent represented by Formula (II-2) is bound as a substituent $R_1$, $R_2$, or $R_3$ through a carbon atom of the 5-membered ring.

Specific examples of the substituent represented by Formula (II-2) include those having the following structural formulae. In the following structural formulae, each hydrogen (H) may be independently substituted as described later.

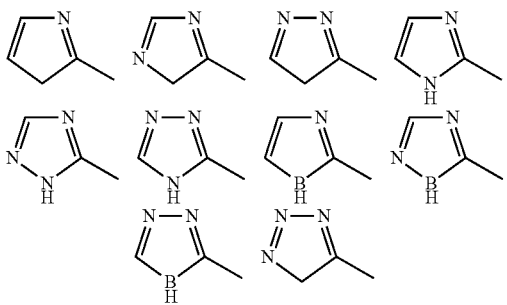

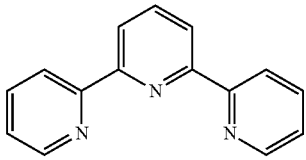 (II-3)

In Formula (II-3), $R_4$ and $R_5$ each independently represent hydrogen or $C_1$-$C_5$ alkyl.

In cases where $R_1$ is a group represented by Formula (II-3), $n_1$ is preferably 2. In cases where $R_2$ is a group represented by Formula (II-3), $n_2$ is preferably 2. In cases where $R_3$ is a group represented by Formula (II-3), $n_3$ is preferably 2.

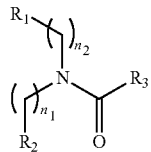 (III)

In Formula (III), each hydrogen may be substituted as described later.

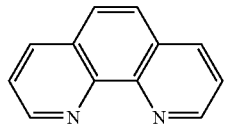 (IV)

In Formula (IV), $R_1$, $R_2$, and $R_3$ each independently represent a group represented by the above Formula (II-1), Formula (II-2), or Formula (II-3), or hydrogen, $C_1$-$C_5$ alkyl, phenyl, or phenylmethoxy. In Formula (IV), $n_1$ and $n_2$ each independently represent 1 or 2);

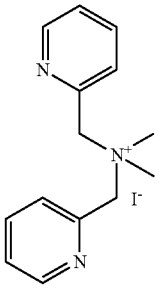 (V)

In Formula (V), each hydrogen may be substituted as described later.

(VI)

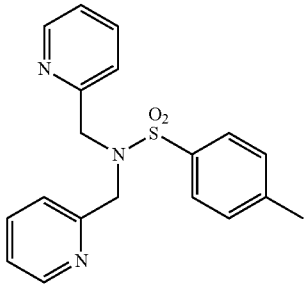 (VII)

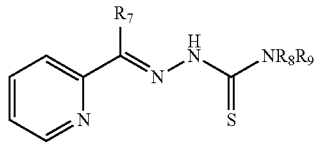 (VIII)

In Formula (VIII), $R_7$ represents the following Formula (II-1). $R_8$ and $R_9$ each independently represent hydrogen, linear, branched or cyclic $C_1$-$C_6$ alkyl, or phenyl.

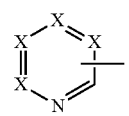 (II-1)

In Formula (II-1), any one of the Xs represents carbon (C) or nitrogen (N), and the other three Xs represent carbon (C). Specific examples of Formula (II-1) are as described above.

In Formula (II-1) and Formula (VIII), each hydrogen may be substituted as described later.

In Formula (II-1), Formula (II-2), Formula (II-3), Formula (III), Formula (V), and Formula (VIII) each hydrogen (H) may be independently substituted with a halogen, alkyl, phenyl, alkoxy, hydroxyl (—OH), carboxyl (—COOH), amino (—NH$_2$), benzamide (—NHCOC$_6$H$_5$), benzylamino (—NHCH$_2$C$_6$H$_5$), tert-butylamide (—NHCO-tBu), neopentylamino (—NHCH$_2$-tBu), —C(═O)OR, —S(═O)$_2$OR, or —OP(═O)(OR)(OR'). R and R' each independently represent hydrogen or alkyl.

Further, each hydrogen (H) in the alkyl, phenyl, alkoxy, "—C$_6$H$_5$" of the benzamide, "—C$_6$H$_5$" of the benzylamino, "-tBu" of the tert-butylamide, and "—CH$_2$—" and "-tBu" of the neopentylamino may be independently substituted with a halogen, hydroxyl, amino, —C(═O)OR, —S(═O)$_2$OR, or —OP(═O)(OR)(OR'). R and R' each independently represent hydrogen or alkyl.

Examples of the halogen include fluorine, chlorine, bromine, and iodine.

The alkyl is preferably $C_1$-$C_{10}$ alkyl, more preferably $C_1$-$C_5$ alkyl. The alkyl may be either linear or branched. The alkyl is preferably linear. Specific examples of the alkyl include methyl, ethyl, propyl, butyl, pentyl, hexyl, heptyl, octyl, nonyl, and decyl.

The alkoxy is preferably $C_1$-$C_{10}$ alkoxy, more preferably $C_1$-$C_5$ alkoxy. The alkoxy may be either linear or branched. The alkoxy is preferably linear. Specific examples of the alkoxy include methoxy, ethoxy, propoxy, butoxy, pentoxy, hexyloxy, heptyloxy, octyloxy, nonyloxy, and decyloxy.

In Formula (I), all of $n_1$, $n_2$, and $n_3$ may be 1; all of $n_1$, $n_2$, and $n_3$ may be 2; or $n_1$, $n_2$, and $n_3$ may be an arbitrary combination of 1 and 2. That is, in Formula (I), zero, one, two, or three "n"s selected from $n_1$, $n_2$, and $n_3$ may be 1, and the remaining "n"s may be 2. However, in cases where one or more selected from $R_1$, $R_2$, and $R_3$ are ethylamine-type substituents, the "n" corresponding to each ethylamine-type substituent "R" is 2. That is, in cases where $R_1$ is an ethylamine-type substituent, $n_1$ is 2; in cases where $R_2$ is an ethylamine-type substituent, $n_2$ is 2; and, in cases where $R_3$ is an ethylamine-type substituent, $n_3$ is 2.

In Formula (I), all of $R_1$, $R_2$, and $R_3$ may be pyridine-type substituents; all of $R_1$, $R_2$, and $R_3$ may be imidazole-type substituents; all of $R_1$, $R_2$, and $R_3$ may be ethylamine-type substituents; or $R_1$, $R_2$, and $R_3$ may be an arbitrary combination of two or more substituents each selected from pyridine-type substituents, imidazole-type substituents, and ethylamine-type substituents. That is, for example, in Formula (I), zero, one, two, or three "R"s selected from $R_1$, $R_2$, and $R_3$ may be pyridine-type substituents, and the remaining "R"s may be imidazole-type substituents or ethylamine-type substituents, or an arbitrary combination thereof. For example, in Formula (I), zero, one, two, or three "R"s selected from $R_1$, $R_2$, and $R_3$ may be imidazole-type substituents, and the remaining "R"s may be pyridine-type substituents or ethylamine-type substituents, or an arbitrary combination thereof. For example, in Formula (I), zero, one, two, or three "R"s selected from $R_1$, $R_2$, and $R_3$ may be ethylamine-type substituents, and the remaining "R"s may be pyridine-type substituents or imidazole-type substituents, or an arbitrary combination thereof.

As an example of the compound represented by Formula (I), a compound in which all of $n_1$, $n_2$, and $n_3$ are 1; all of $R_1$, $R_2$, and $R_3$ are pyridine-type substituents; all of the Xs are carbon; and none of the hydrogens is substituted; is shown by the following Formula. This compound is tris(2-pyridylmethyl)amine (L6 in Examples). The compound can be synthesized according to a normal synthesis method, or can be purchased from Sigma-Aldrich.

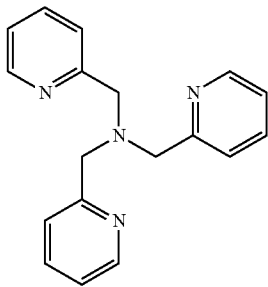 [SMILES: c1ccc(CN(Cc2ccccn2)Cc2ccccn2)nc1]

Other examples of the compound represented by Formula (I) include the following compounds. These compounds can be similarly synthesized.

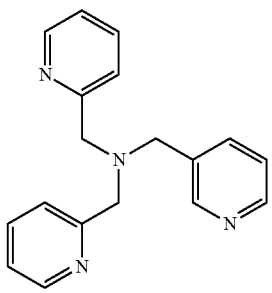

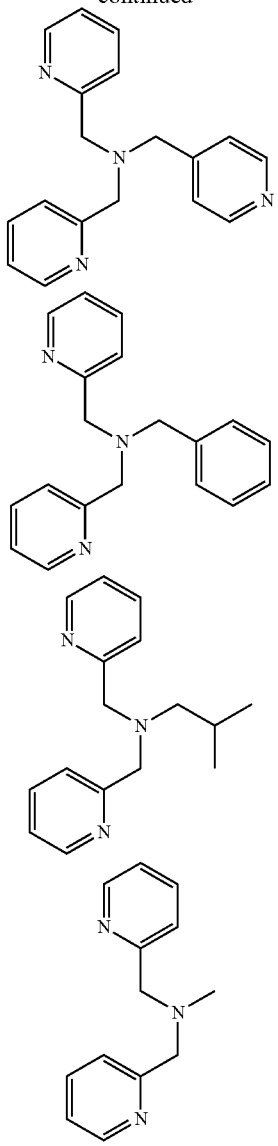

As an example of the compound represented by Formula (III), a compound in which none of the hydrogens is substituted is shown below. This compound is 2,2':6',2"-terpyridine (L18 in Examples). The compound can be synthesized according to a normal synthesis method, or can be purchased from Tokyo Chemical Industry Co., Ltd.

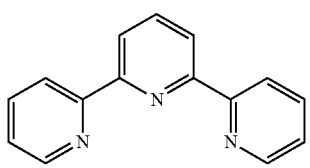 [SMILES: c1ccc(-c2cccc(-c3ccccn3)n2)nc1]

As examples of the compound represented by Formula (V), the following compounds are shown. These compounds can be synthesized according to normal synthesis methods. L2 can be purchased from Sigma-Aldrich; L3 can be purchased from Sigma-Aldrich; L16 can be purchased from Tokyo Chemical Industry Co., Ltd.; and L17 can be purchased from Dojindo Laboratories.
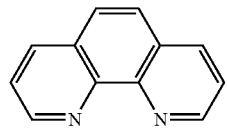
L2 in Examples
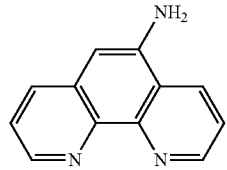
L3 in Examples
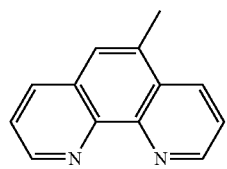
L16 in Examples
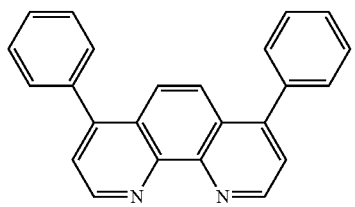
L17 in Examples
As examples of the compound represented by Formula (IV), the following compounds are shown. These compounds can be synthesized according to the methods in Reference Examples described later.
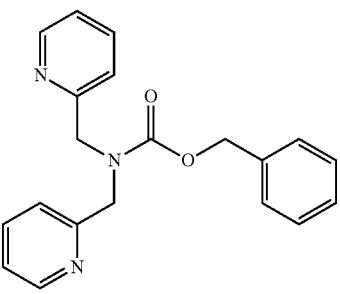
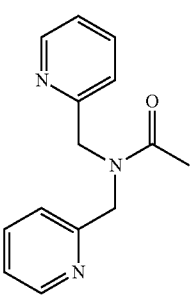
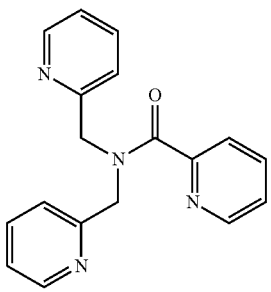
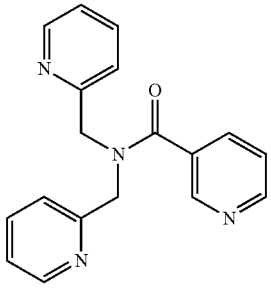
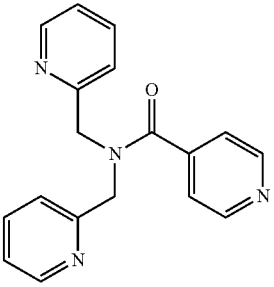

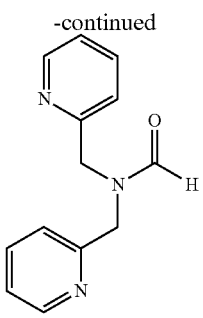

As an example of the compound represented by Formula (VIII), compounds in which $R_7$ is pyridine; $R_8$ and $R_9$ are methyl or cyclohexyl; and none of the hydrogens is substituted; are shown by the following Formulae. These compounds are di-2-pyridylketone 4,4-dimethyl-3-thiosemicarbazone (DP44mT in Example 8) and di-2-pyridylketone-4-cyclohexyl-4-methyl-3-thiosemicarbazone (DpC in Example 9). The compound can be synthesized according to a normal synthesis method.

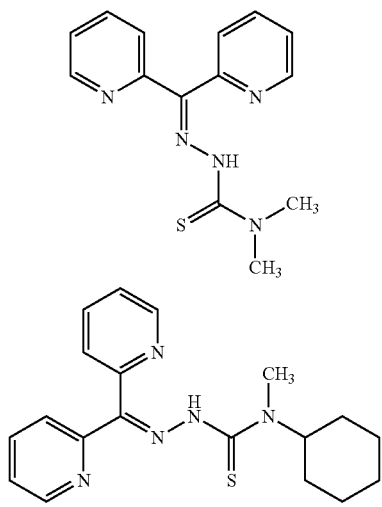

In the present invention, the active ingredient may be a free compound; a salt or a metal complex thereof; or a mixture of these.

The salt is not limited as long as it is a pharmaceutically acceptable salt. Specific examples of the salt include, as salts for acidic groups, ammonium salt; salts with alkali metals such as sodium and potassium; salts with alkali earth metals such as calcium and magnesium; aluminum salt; zinc salt; salts with organic amines such as triethylamine, ethanolamine, morpholine, pyrrolidine, piperidine, piperazine, and dicyclohexylamine; and salts with basic amino acids such as arginine and lysine. Specific examples of the salt include, as salts for basic groups, salts with inorganic acids such as hydrochloric acid, sulfuric acid, phosphoric acid, nitric acid, and hydrobromic acid; salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid; and salts with organic sulfonic acids such as methanesulfonic acid, benzenesulfonic acid, and p-toluenesulfonic acid. As the salt, a single kind of salt may be used, or a combination of two or more kinds of salts may be used.

Examples of the metal complex include metal complexes of zinc, iron, copper, cobalt, nickel, and manganese. The metal complex is preferably a zinc complex.

As the active ingredient, a single kind of compound may be used, or a combination of two or more kinds of compounds may be used.

As the active ingredient, a commercially available compound may be used, or a synthesized compound may be used as appropriate.

The active ingredient may be either a purified compound or an unpurified compound. For example, the active ingredient may be used after purification to a desired purity, if necessary. The purity of the active ingredient may be, for example, not less than 30% (w/w), not less than 50% (w/w), not less than 70% (w/w), not less than 90% (w/w), or not less than 95% (w/w). The purification may be carried out by, for example, a known method. Examples of such a method include ion-exchange chromatography, reversed phase chromatography, affinity chromatography, gel filtration chromatography, membrane separation, and crystallization.

The antimalarial drug of the present invention comprises the above-described active ingredients. The antimalarial drug of the present invention may be composed of only the above-described active ingredients, or may also contain another component. The "another component" is not limited as long as it is pharmaceutically acceptable. Examples of the "another component" include those used as components to be contained in pharmaceuticals.

The antimalarial drug of the present invention may be, for example, formulated into an arbitrary dosage form. Examples of the dosage form include liquids, suspensions, powders, tablets, balls, capsules, and injection solutions. For the formulation, one or more of pharmaceutically acceptable additives such as vehicles, binders, disintegrators, lubricants, stabilizers, corrigents, flavoring agents, perfumes, diluents, and surfactants may be used.

The antimalarial drug of the present invention may also contain another antimalarial component. Examples of such a component include mefloquine, chloroquine, amodiaquin, quinine, artemisinin, atovaquone, Fansidar, halofantrine, proguanil, and doxycycline, and derivatives thereof.

The concentration of the active ingredient in the antimalarial drug of the present invention is not limited as long as malaria can be prevented and/or treated using the antimalarial drug of the present invention. The concentration may be appropriately set depending on conditions such as the type of the active ingredient, the formulation of the antimalarial drug of the present invention, and the administration mode of the antimalarial drug of the present invention. Although the concentration of the active ingredient in the antimalarial drug of the present invention is not limited, it may be, for example, not more than 100% (w/w), not more than 10% (w/w), or not more than 1% (w/w). Although the concentration of the active ingredient in the antimalarial drug of the present invention is not limited, it may be, for example, not less than 0.01% (w/w), not less than 0.1% (w/w), or not less than 1% (w/w).

By administration of the antimalarial drug of the present invention to a subject, prevention and/or treatment of malaria can be carried out. Thus, the antimalarial drug of the present invention is, in other words, a pharmaceutical composition for prevention and/or treatment of malaria. The present invention also provides a method for preventing and/or treating malaria, comprising administration of the antimalarial drug of the present invention to a subject.

The type of the malaria to be prevented and/or treated with the antimalarial drug of the present invention is not limited. Specific examples of the malaria include falciparum malaria, vivax malaria, ovale malaria, and malariae malaria, and malaria caused by mixed infection with two or more types of malaria parasites. The antimalarial drug of the present invention may be applied to any of the types of malaria described above.

The antimalarial drug of the present invention may be administered to the subject as it is, or after dilution, dissolution, dispersion, or the like in a pharmaceutically acceptable solvent such as water, physiological saline, or a buffer. Needless to say, the antimalarial drug after such dilution, dissolution, dispersion, or the like is included within the scope of the antimalarial drug of the present invention. Examples of the administration mode include, but are not limited to, oral administration; invasive administration such as injection; and transdermal administration. The administration mode may be set depending on conditions such as the formulation of the antimalarial drug of the present invention.

The dose of the antimalarial drug of the present invention may be appropriately set depending on conditions such as the content of the active ingredient, usage, age, sex, and severity of symptoms. The dose of the antimalarial drug of the present invention may be, for example, preferably 0.1 mg/kg body weight/day to 500 mg/kg body weight/day, more preferably 1 mg/kg body weight/day to 100 mg/kg body weight/day, in terms of the dose of the active ingredient. The antimalarial drug of the present invention may be administered once per day, or dividedly in a plurality of times per day. Alternatively, the antimalarial drug of the present invention may be administered once per several days or several weeks. The dose of the antimalarial drug, in terms of the dose of the active ingredient, may be either constant or variable among the times of administration.

The antimalarial drug of the present invention may be administered either alone or in combination with one or more other drugs. For example, the antimalarial drug of the present invention may be used in combination with one or more other antimalarial drugs. Examples of the other antimalarial drugs include pharmaceuticals containing the other antimalarial components described above.

EXAMPLES

The present invention is described below more concretely by way of Examples.

Experiment 1

Search for Metal Chelators that Exhibit Antimalarial Activity

Compounds that chelate metal ions in various modes (L1 to L25 in FIG. 1) were selected, and their antimalarial activities were evaluated by LDH assay. Since infection with malaria causes an increase in the LDH activity, the evaluation can be made based on the criteria that the lower the detected LDH activity, the higher the antimalarial activity. The names of the compounds L1 to L25 are as follows.
L1: 2,2'-Bipyridyl
L2: (1,10)-Phenanthrolin
L3: (1,10)-Phenanthrolin-5-amine
L4: Di-(2-picolyl)amine
L5: 2-(Bis-(2-pyridylmethyl)amine ethanol
L6: Tris(2-pyridylmethyl)amine
L7: N,N,N',N'-Tetrakis(2-pyridylmethyl)ethylenediamine
L8: Ethylenediaminetetraacetic acid
L9: N,N,N',N'-Tetramethylethylenediamine
L10: 1,4,7-Triazacyclononane
L11: N,N,N',N'',N''-Pentamethyldiethylenetriamine
L12: 1,1,4,7,10,10-Hexamethyltriethylenetetramine
L13: Tris[2-(dimethylamino)ethyl]amine
L14: 1,4,7-Trimethyl-1,4,7-triazacyclononane
L15: 1,4,7,10-Tetraazacyclododecane
L16: 5-Methyl-1,10-phenanthroline
L17: 4,7-Diphenyl-1,10-phenanthroline
L18: 2,2':6',2''-Terpyridine
L19: 2,6-Bis(2-benzimidazolyl)pyridine
L20: 2,4,6-Tri(2-pyridyl)-1,3,5-triazine
L21: Potassium tris(1-pyrazolyl)borohydride
L22: Potassium tri(3,5-dimethyl-1-pyrazolyl)borohydride
L23: 29H,31H-Phthalocyanine
L24: Disodium phthalocyanine
L25: Nitrilotriacetic acid The LDH assay was carried out according to the following procedure. That is, 0.5 µL of a solution of each compound in DMSO was added to 100 µL of a culture liquid of erythrocytes (88% RPMI solution; 2% erythrocytes, provided by the Japanese Red Cross Society; and 10% human serum, provided by the Japanese Red Cross Society) infected with falciparum malaria parasites (*Plasmodium falciparum* 3D7 strain) (infection rate of erythrocytes, 0.3%). The resulting culture liquid was subjected to culture in a 96-well plate under an atmosphere of 5% $CO_2$, 5% $O_2$, and 90% $N_2$ at 37° C. for three days. Subsequently, the culture liquid was cooled at −80° C. for three hours, and then returned to room temperature. After addition of 150 µL of an LDH enzyme reaction liquid (0.15 mg/mL diaphorase, 37.5 µL/mL of 50% sodium lactate, 0.17 mg/mL NBT, 0.11 mg/mL APAD, 0.16 mL/mL of 1 M Tris-HCl (pH 8), and 8.3 µL/mL of Tween 20), the absorbance at 620 nm was measured.

Figure 2:
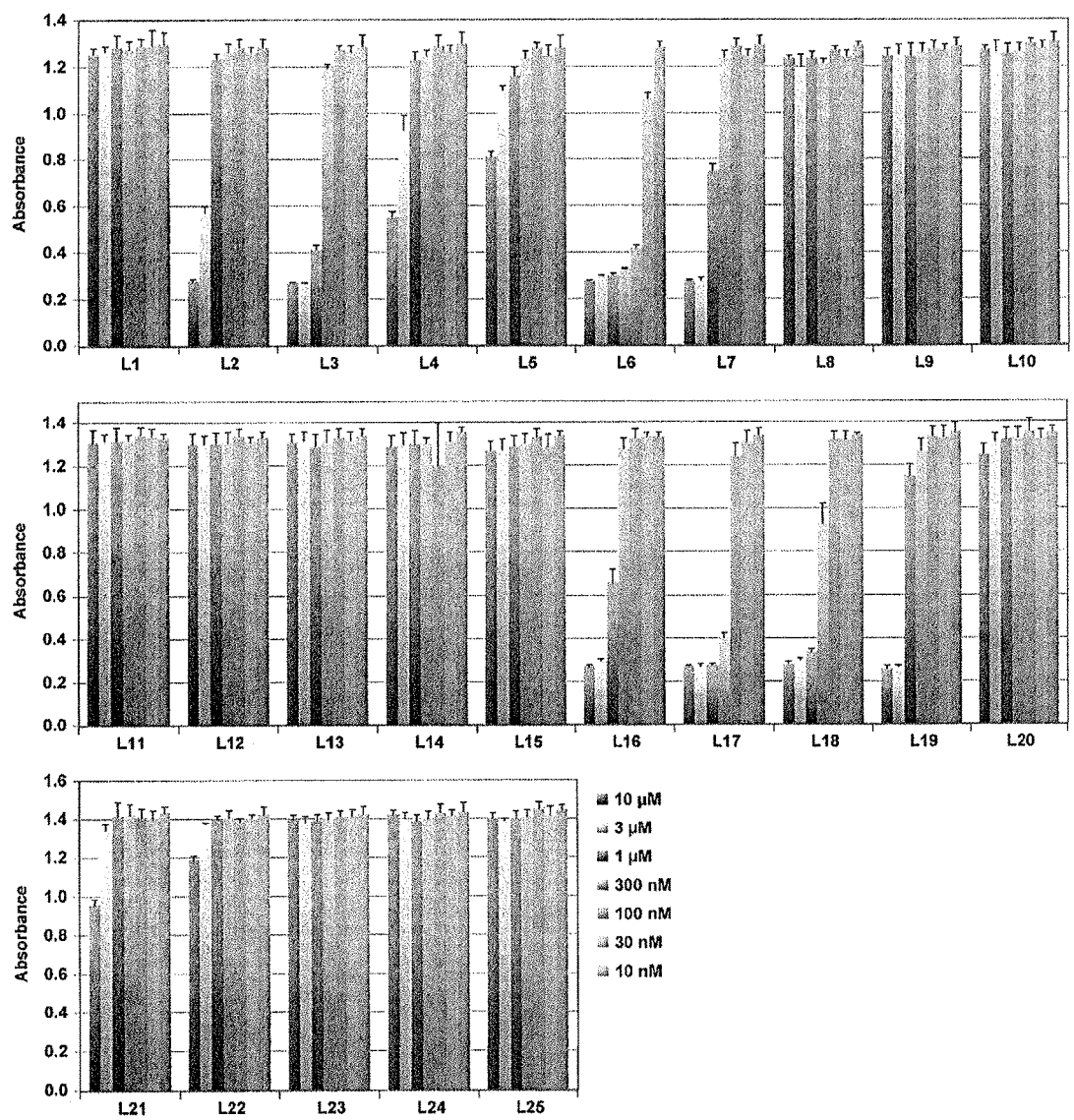
FIG. 2 is a diagram showing the antimalarial activities of metal chelators as measured by LDH assay. For each of L1 to L25, data obtained at 10 nM, 30 nM, 100 nM, 300 nM, 1 µM, 3 µM, and 10 µM are shown from right to left.

As a result, L6 (tris(2-pyridylmethyl)amine) was found to show remarkable antimalarial activity (FIG. 2). In addition, L17 (4,7-diphenyl-1,10-phenanthroline) and L18 (2,2':6',2''-terpyridine) were found to show relatively strong antimalarial activity (FIG. 2). As a result of calculation of the $IC_{50}$ value for the antimalarial activity based on the LDH assay, it was found that the $IC_{50}$ value of L6 (=about 31 nM) is close to the $IC_{50}$ values of existing antimalarial drugs (chloroquine, about 45 nM; artemisinin, about 16 nM). Further, L6 was found to exhibit antimalarial activity also against a chloroquine-resistant strain.

Experiment 2

Analysis of Antimalarial Action Mechanism

Figure 3:
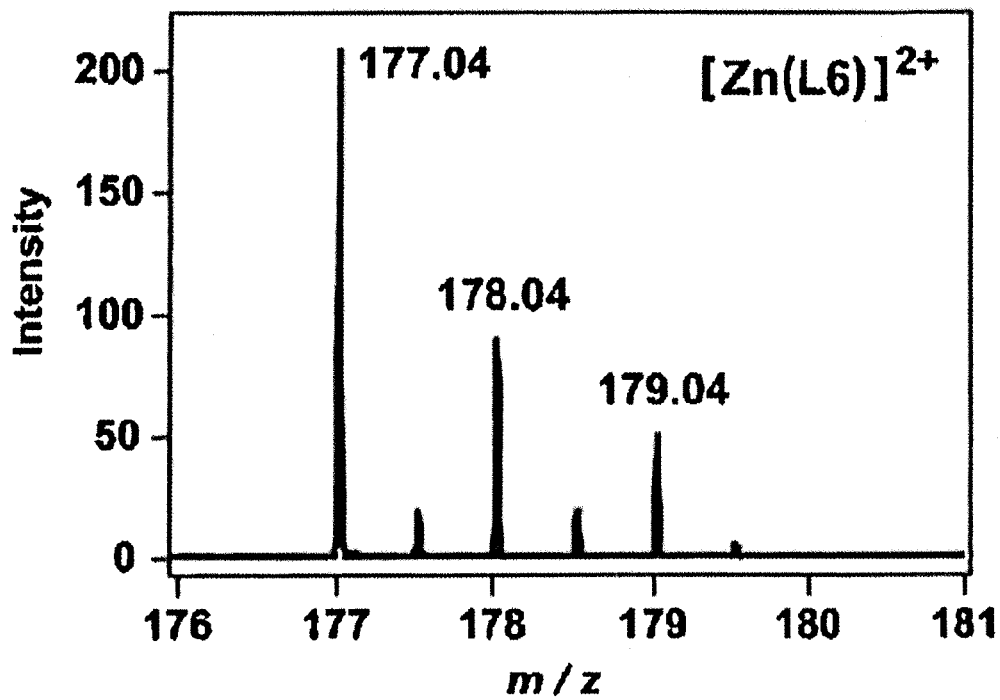
FIG. 3 is a diagram showing the detection result for a zinc complex of tris(2-pyridylmethyl)amine by ESI mass measurement.

By the same procedure as in Experiment 1, erythrocytes infected with malaria were treated with L6 (about 40 nM) together with iron ion (about 50 µM), copper ion (about 1 µM), or zinc ion (about 10 µM), and the antimalarial activity was evaluated by LDH assay. As a result, suppression of the antimalarial activity was found to some extent in the case where excess zinc ion was added to L6. Further, as a result of detection of zinc complex by ESI mass measurement, it was found that L6 forms stable zinc complex at a ratio of L6: zinc ion of 1:1 (FIG. 3).

Experiment 3

Evaluation of Cytotoxicity

After treating various kinds of cells (HEK293T: human embryonic kidney cells; HeLa: human cervical cancer cells; NIH3T3: mouse fibroblast cells; tsNRK: rat kidney cells; and 3Y1: rat fibroblasts) with a metal chelator for 48 hours, the cytotoxicities of the cells were evaluated by WST-8 assay. As a result, it was found that the concentration at which L6 exhibits antimalarial activity is about 170 times lower ($IC_{50}$ value=about 31 nM) than the concentration at which toxicity is exerted ($IC_{50}$ value=about 5.08 to 5.61 μM) on human cells (HEK293T and HeLa) (Table 1).

TABLE 1

| Cell | L3 | L6 | L7 |
|---|---|---|---|
| HEK293T | 0.49/0.47 | 5.08/5.31 | 1.99/3.14 |
| HeLa | — | 5.61/5.16 | 5.53/4.96 |
| NIH3T3 | — | 1.80/1.95 | 1.66/1.79 |
| tsNRK | 6.12/3.08 | 1.88/1.90 | 1.84/2.09 |
| 3Y1 | 0.73/0.67 | 2.42/3.87 | 5.11/4.93 |

$IC_{50}$ value (μM)
1st measurement/2nd measurement

Experiment 4

In Vivo Analysis 1 (Evaluation of Effect to Suppress Malaria Infection)

Figure 4:
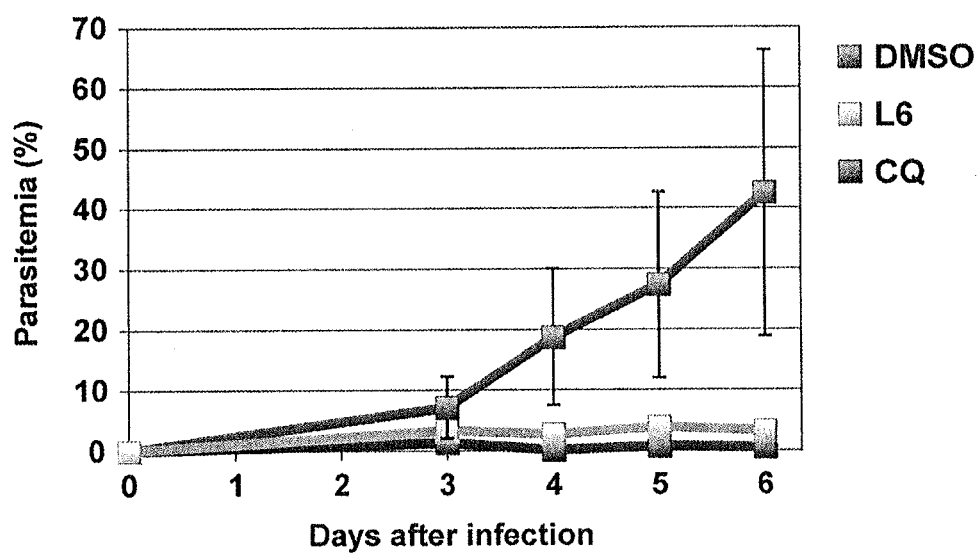
FIG. 4 is a diagram showing the malaria infection-suppressing effect of tris(2-pyridylmethyl)amine. "L6" represents tris(2-pyridylmethyl)amine, and "CQ" represents chloroquine.

To mice (7 weeks old, Balb/c, male), erythrocytes infected with mouse malaria parasites (*Plasmodium berghei* ANKA strain) (total number of erythrocytes per mouse, about $10^7$; rate of malaria-infected erythrocytes, 0.3%) were intraperitoneally injected. L6 was administered (20 mg/kg, intraperitoneal injection) to each of the thus obtained malaria-infected mice, and the rate of malaria-infected erythrocytes was measured. As a result, on Day 2 to Day 6 after the infection, the infection rate tended to increase in the negative control to which only DMSO was administered. On the other hand, the infection rate could be remarkably suppressed in the case where L6 was administered (FIG. 4). The effect of L6 to reduce the infection rate was almost equivalent to the effect of an existing drug, chloroquine (CQ). That is, L6 was found to exhibit antimalarial activity also in vivo.

Experiment 5

In Vivo Analysis 2 (Evaluation of Life-prolonging Effect after Infection with Malaria)

Figure 5:
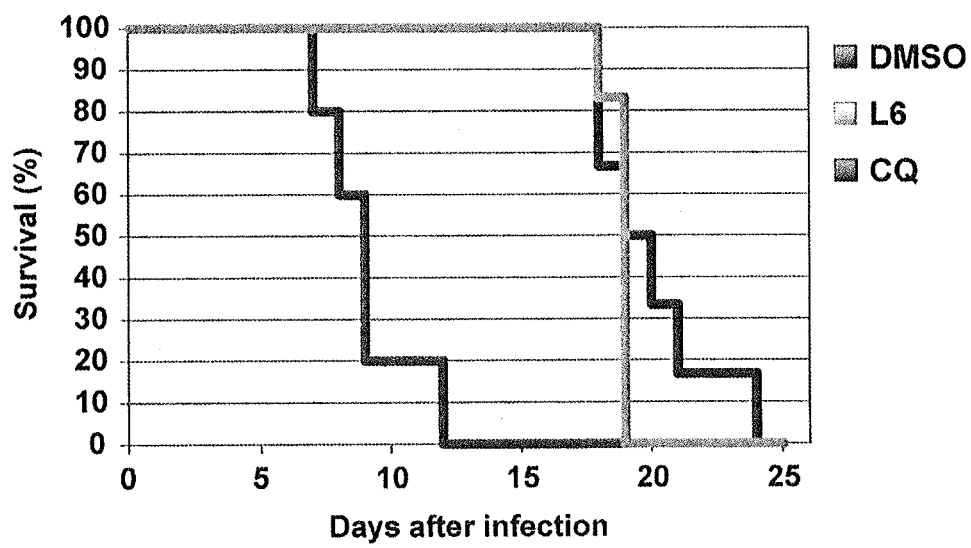
FIG. 5 is a diagram showing the life-prolonging effect of tris(2-pyridylmethyl)amine after infection with malaria. "L6" represents tris(2-pyridylmethyl)amine, and "CQ" represents chloroquine.

After administration of L6 to malaria-infected mice (20 mg/kg, intraperitoneal injection), changes in the number of surviving individuals were investigated. As a result, a remarkable life-prolonging effect could be observed after the administration of L6 (FIG. 5). The life-prolonging effect by L6 was almost equivalent to the effect of an existing drug, chloroquine (CQ). That is, L6 was again found to exhibit antimalarial activity also in vivo.

As described above, compounds such as L6 (tris(2-pyridylmethyl)amine) were discovered as novel antimalarial drugs. These compounds are useful for prevention and/or treatment of malaria.

Experiment 6

Evaluation of Antimalarial Activity and Cytotoxicity of L6 Forming Metal Complex According to the same procedure as in Experiment 1, the antimalarial activities of metal complexes (M-L6) synthesized by mixing various kinds of metal ions (MSO4: M=Zn, Fe, Cu, Co, Ni, or Mn) with L6 at a molar ratio of 1:1 were evaluated by LDH assay. As a result, it was found that, compared to the antimalarial activity produced by L6 alone, the antimalarial activities produced by the metal complexes M-L6 (M=Fe, Cu, Co, Ni, and Mn) are uniformly low. On the other hand, in the case of the zinc complex Zn-L6, the antimalarial activity ($IC_{50}$) was almost the same as that in the case of L6 alone. Thus, it is thought that the influence of formation of zinc complex on the antimalarial activity is very small (Table 2). It was also found that L6 and the zinc complex Zn-L6 can exert antimalarial activity also against the K1 strain and the Dd2 strain, which are drug-resistant malaria parasites, at the same level of concentration ($IC_{50}$=80 to 160 nM).

TABLE 2

| | $IC_{50}$ (μM) | | |
|---|---|---|---|
| | 3D7 | K1 | Dd2 |
| L6 | 0.084 | 0.082 | 0.144 |
| Zn-L6 | 0.093 | 0.089 | 0.166 |
| Fe-L6 | 0.19 | — | — |
| Cu-L6 | 0.12 | — | — |
| Co-L6 | 0.55 | — | — |
| Ni-L6 | 0.74 | — | — |
| Mn-L6 | 0.11 | — | — |

— not tested

Subsequently, the following cell types: HL60 (human promyelocytic leukemia cells), HeLa (human cervical cancer cells), C3H10T1/2 (murine multipotential mesenchymal cells), and HEK293 (human embryonic kidney 293 cells); were treated with metal complexes M-L6 (M=Zn, Fe, Cu, Co, Ni, and Mn) for 48 hours, and then subjected to WST-8 assay to perform evaluation of the cytotoxicity of each kind of metal complex. As a result, it was revealed that L6 and the metal complexes M-L6 (M=Fe, Cu, Co, Ni, and Mn) show cytotoxicity ($IC_{50}$) within the concentration range of several micromolar to several ten micromolar. On the other hand, it was revealed that the zinc complex Zn-L6 does not show cytotoxicity even at a concentration of not less than 100 μM (Table 3).

TABLE 3

| | $IC_{50}$ (μM) | | | |
|---|---|---|---|---|
| | HL60 | HeLa | C3H10T1/2 | HEK293 |
| L6 | 1.8 | 5.8 | 5.7 | 6.0 |
| Zn-L6 | >100 | >100 | >100 | >100 |
| Fe-L6 | 4.8 | 9.5 | 9.6 | 6.1 |
| Cu-L6 | 5.0 | 13.0 | 12.0 | 6.0 |
| Co-L6 | 6.6 | 18.0 | 18.0 | 20.5 |
| Ni-L6 | 16.0 | 32.0 | 54.0 | 47.6 |
| Mn-L6 | 1.5 | 4.5 | 4.2 | 3.7 |

Experiment 7

Figure 6:
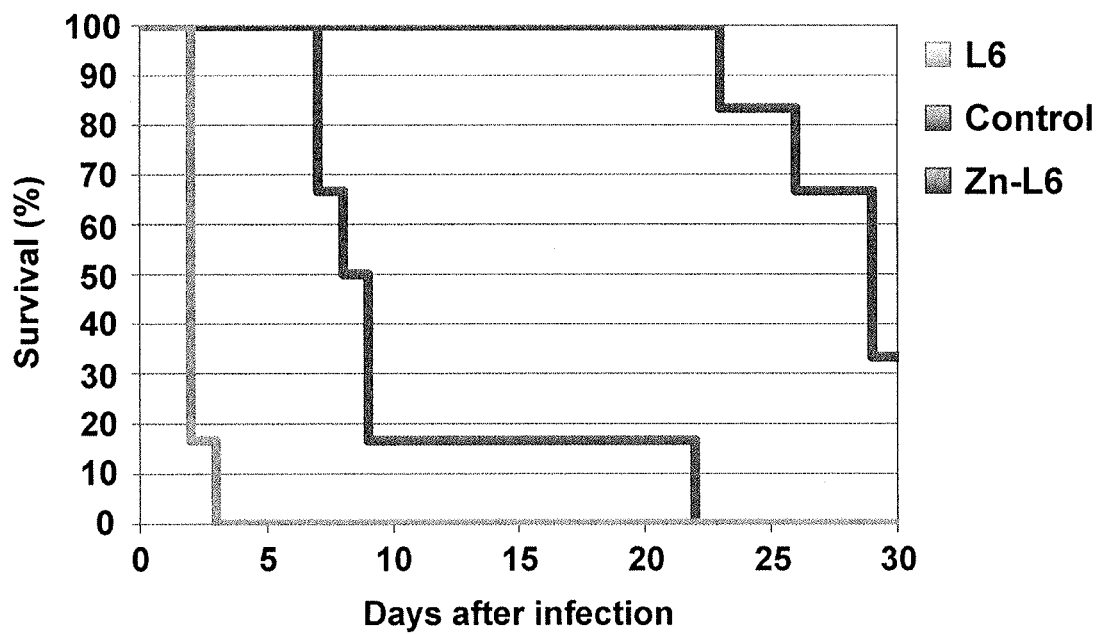
FIG. 6 is a diagram showing the life-prolonging effects of tris(2-pyridylmethyl)amine and its zinc complex after infection with malaria. "L6" represents tris(2-pyridylmethyl)amine; "Zn-L6" represents a zinc complex of tris(2-pyridylmethyl)amine; and "Control" represents use of only a buffer.

Evaluation of Life-Prolonging Effect of Zinc Complex-Forming L6 Orally Administered to Malaria-Infected Mice To malaria-infected mice obtained by the same procedure as in Experiment 4, an aqueous solution of L6 or the zinc complex Zn-L6 was orally administered (at a dose of 200 mg/kg on Day 1, Day 3, and Day 6; N=6), and changes in the number of surviving individuals were investigated. As a result (FIG. 6), it was found that the influence of toxicity appears when L6 alone is administered at the high concentration used in the present experiment. On the other hand, in the case of the zinc complex Zn-L6, a significantly better life-prolonging effect than in the control could be observed, and completely cured mice, in which the infection rate of malaria was 0%, could be found. That is, it is thought that, by formation of metal complex with zinc ion, L6 can remarkably suppress the toxicity in vivo while sufficiently maintaining the antimalarial activity.

Experiment 8

Evaluation Antimalarial Activities of L18 and Dp44mT

According to the same procedure as in Experiment 1, the antimalarial activities of L18 and di-2-pyridylketone 4,4-dimethyl-3-thiosemicarbazone (Sigma) against the malaria parasite 3D7 strain and the drug-resistant malaria parasite K1 strain were evaluated by LDH assay. As a result, those compounds were found to exhibit remarkable antimalarial activities against both malaria parasites (L18: ICso =about 280 nM (3D7) and about 120 nM (K1); di-2-pyridylketone 4,4-dimethyl-3-thiosemicarbazone: $IC_{50}$=about 4 nM (3D7) and about 3 nM (K1)).

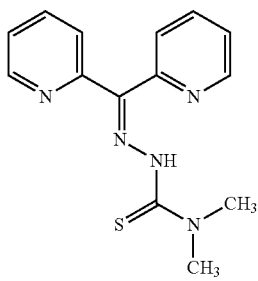 [SMILES: CN(C)C(=S)NN=C(c1ccccn1)c1ccccn1]

di-2-pyridylketone 4,4-dimethyl-3-thiosemicarbazone

Experiment 9

Evaluation Antimalarial Activities of Dp44mT and DpC

According to the same procedure as in Experiment 1, the antimalarial activities of di-2-pyridylketone 4,4-dimethyl-3-thiosemicarbazone (Dp44mT) (Sigma) and di-2-pyridylketone-4-cyclohexyl-4-methyl-3-thiosemicarbazone (DpC) (Sigma) against the malaria parasite 3D7 strain were evaluated by LDH assay. As a result, those compounds were found to exhibit remarkable antimalarial activities against the malaria parasite (di-2-pyridylketone 4,4-dimethyl-3-thiosemicarbazone: $IC_{50}$=about 2 nM (3D7); and di-2-pyridylketone-4-cyclohexyl-4-methyl-3-thiosemicarbazone: $IC_{50}$=about 2 nM (3D7)).

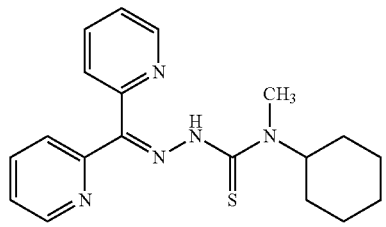 [SMILES: CN(C(=S)NN=C(c1ccccn1)c1ccccn1)C1CCCCC1]

di-2-pyridylketone-4-cyclohexyl-4-methyl-3-thiosemicarbazone

Reference Example 1

Synthesis of N,N-Bis(pyridin-2-ylmethyl)isobutyramide (WA-009)

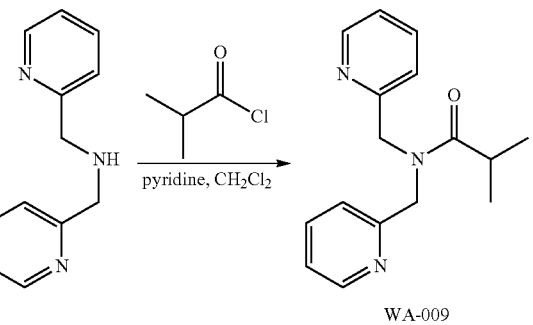

WA-009

To a stirred solution of bis(pyridin-2-ylmethyl)amine (19.9 mg, 0.1 mmol) and pyridine (16.1 µl, 0.2 mmol) in 1 mL of dichloromethane, isobutyryl chloride (16.0 µL, 0.15 mmol) was added under nitrogen atmosphere at room temperature. After stirring the resulting mixture for 15 minutes, the mixture was concentrated under vacuum. The resulting residue was purified by $SiO_2$ column chromatography (chloroform:MeOH=5:1), to obtain WA-009 (12.1 mg, 45%) as a colorless oily product.

WA-009: $^1$H NMR (500 MHz, $CDCl_3$) δ 1.16 (d, J=6.9 Hz, 6H), 2.87 (qq, J=6.9 Hz, 1H), 4.75 (s, 2H), 4.79 (s, 2H), 7.16 (bdd, J=8.0, 5.0 Hz, 1H), 7.17 (d, J=8.0 Hz, 1H), 7.20 (bdd, J=8.0, 5.0 Hz, 1H), 7.29 (d, J=8.0 Hz, 1H), 7.64 (ddd, J=8.0, 8.0, 1.5 Hz, 1H), 7.67 (ddd, J=8.0, 8.0, 1.5 Hz, 1H), 8.49 (bdd, J=5.0, 1.5 Hz, 1H), 8.57 (bdd, J=5.0, 1.5 Hz, 1H).
$^{13}$C NMR (125 MHz, $CDCl_3$) δ 19.6, 30.4, 51.4, 52.9, 120.4, 122.2, 122.3, 122.4, 136.8, 136.9, 149.0, 149.8, 156.6, 157.6, 178.2.

Reference Example 2

Synthesis of Benzyl Bis(pyridin-2-ylmethyl)carbamate (WA-011)

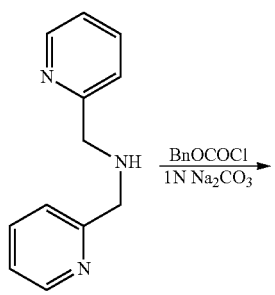

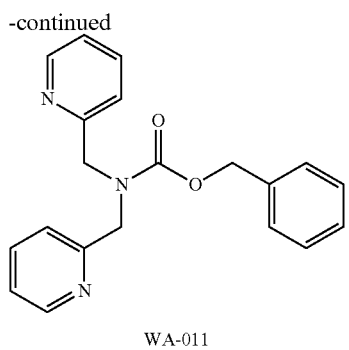

WA-011

To a stirred solution of bis(pyridin-2-ylmethyl)amine (19.9 mg, 0.1 mmol) in 0.5 mL of aqueous 1N $Na_2CO_3$ solution, benzyl chloroformate (21.1 µL, 0.15 mmol) was added at room temperature. After stirring the resulting mixture for 15 minutes, the mixture was diluted with ethyl acetate, and the organic layer was washed with water and brine, followed by drying over $Na_2SO_4$ and concentration under vacuum. The resulting residue was purified by $SiO_2$ column chromatography (chloroform:MeOH=10:1), to obtain WA-011 (23.0 mg, 69%) as a colorless oily product.

WA-011: $^1$H NMR (500 MHz, $CDCl_3$) δ 4.69 (s, 2H), 4.74 (s, 2H), 5.20 (s, 2H), 7.11-7.19 (m, 3H), 7.23-7.34 (m, 6H), 7.58 (bdd, J=7.5, 7.5 Hz, 1H), 7.64 (bdd, J=7.5, 7.5 Hz, 1H), 8.52 (bs, 2H).

$^{13}$C NMR (125 MHz, $CDCl_3$) δ 52.3, 52.8, 67.5, 121.0, 122.0, 122.1, 122.3, 127.8, 127.9, 128.4, 136.4, 136.6, 136.7, 149.3, 149.3, 156.7, 157.3, 157.5.

Reference Example 3

Synthesis of N,N-Bis(pyridin-2-ylmethyl)nicotinamide (WA-014)

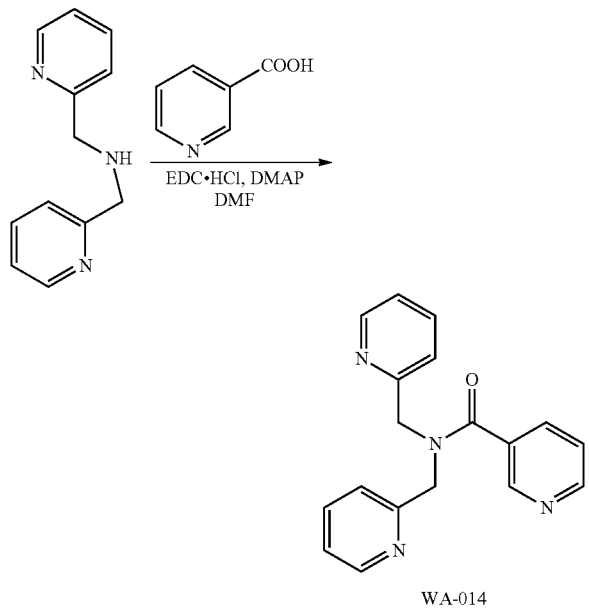

WA-014

To a stirred solution of bis(pyridin-2-ylmethyl)amine (19.9 mg, 0.1 mmol), 4-dimethylaminopyridine (DMAP) (1 mg), and 3-(3-dimethylaminopropyl)-1-ethylcarbodiimide (EDC) hydrochloride (34.5 mg, 0.18 mmol) in 1 mL of dehydrated DMF, nicotinic acid (14.8 mg, 0.12 mmol) was added under nitrogen atmosphere at room temperature. After stirring the resulting mixture for three days, the mixture was concentrated under vacuum, and diluted with ethyl acetate. The organic layer was washed with water and brine, and then dried over $Na_2SO_4$, followed by concentration under vacuum. The resulting residue was purified by diol column chromatography (chloroform), to obtain WA-014 (19.2 mg, 63%) as a colorless oily product.

WA-014: $^1$H NMR (500 MHz, $CDCl_3$) δ 4.68 (s, 2H), 4.87 (s, 2H), 7.16 (d, J=7.5 Hz, 1H), 7.21 (bs, 2H), 7.30 (dd, J=7.5, 4.5 Hz, 1H), 7.42 (bd, J=7.5 Hz, 1H), 7.63-7.72 (m, 2H), 7.97 (ddd, J=7.5, 1.5, 1.5 Hz, 1H), 8.54 (bd, J=3.5 Hz, 1H), 8.60 (bd, J=3.5 Hz, 1H), 8.62 (bd, J=4.5 Hz, 1H), 8.86 (bd, J=1.5 Hz, 1H). $^{13}$C NMR (125 MHz, $CDCl_3$) δ 50.5, 54.3, 121.7, 122.4, 122.7, 123.2, 132.0, 135.0, 136.5, 136.8, 148.0, 149.3, 150.0, 150.7, 155.8, 156.6, 170.0.

Reference Example 4

Synthesis of N,N-Bis(pyridin-2-ylmethyl)isonicotinamide (WA-015)

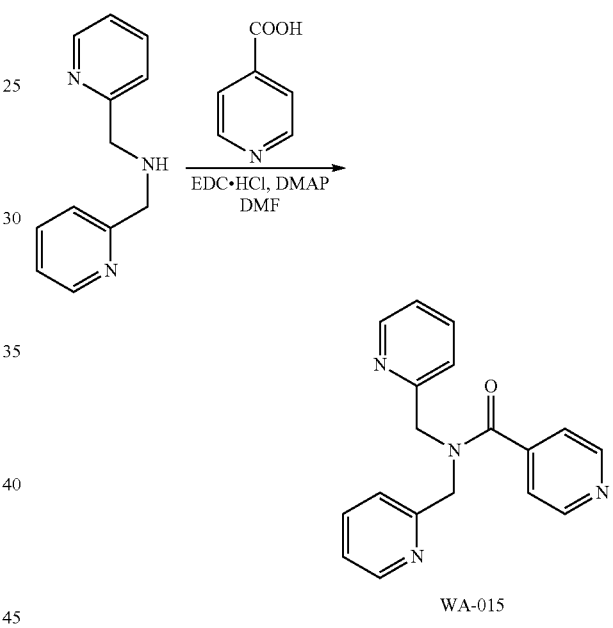

WA-015

To a stirred solution of bis(pyridin-2-ylmethyl)amine (19.9 mg, 0.1 mmol), 4-dimethylaminopyridine (DMAP) (1 mg), and 3-(3-dimethylaminopropyl)-1-ethylcarbodiimide (EDC) hydrochloride (34.5 mg, 0.18 mmol) in 1 mL of dehydrated DMF, isonicotinic acid (14.8 mg, 0.12 mmol) was added under nitrogen atmosphere at room temperature. After stirring the resulting mixture for four days, the mixture was concentrated under vacuum, and diluted with ethyl acetate. The organic layer was washed with water and brine, and then dried over $Na_2SO_4$, followed by concentration under vacuum. The resulting residue was purified by diol column chromatography (chloroform), to obtain WA-015 (19.9 mg, 65%) as a colorless oily product.

WA-015: $^1$H NMR (500 MHz, $CDCl_3$) δ 4.62 (s, 2H), 4.85 (s, 2H), 7.13 (bd, J=7.5 Hz, 1H), 7.18-7.24 (m, 2H), 7.40 (bd, J=7.5 Hz, 1H), 7.49 (dd, J=5.0, 1.5 Hz, 1H), 7.66 (ddd, J=8.0, 7.5, 1.5 Hz, 1H), 7.68 (ddd, J=8.0, 7.5, 1.5 Hz, 1H), 8.54 (bd, J=4.0 Hz, 1H), 8.60 (bd, J=4.0 Hz, 1H), 8.64 (dd, J=5.0, 1.5 Hz, 1H).

$^{13}$C NMR (125 MHz, $CDCl_3$) δ 50.2, 54.0, 121.3, 121.7, 122.5, 122.7, 136.7, 136.8, 143.7, 149.3, 150.0, 150.1, 155.7, 156.5, 170.1.

Reference Example 5

Synthesis of N,N-Bis(pyridin-2-ylmethyl)formamide (WA-016)

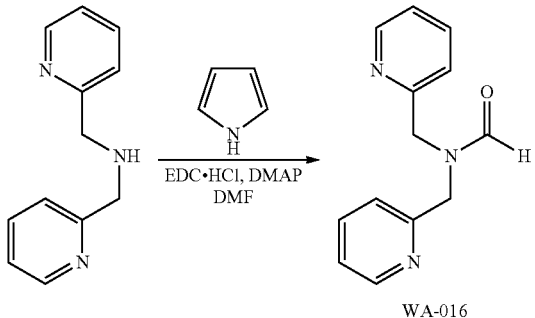

To a stirred solution of bis(pyridin-2-ylmethyl)amine (19.9 mg, 0.1 mmol), 4-dimethylaminopyridine (DMAP) (1 mg), and 3-(3-dimethylaminopropyl)-1-ethylcarbodiimide (EDC) hydrochloride (34.5 mg, 0.18 mmol) in 1 mL of dehydrated DMF, pyrrol-2-carboxylic acid (13.3 mg, 0.12 mmol) was added under nitrogen atmosphere at room temperature. After stirring the resulting mixture for four days, the mixture was concentrated under vacuum, and diluted with ethyl acetate. The organic layer was washed with water and brine, and then dried over $Na_2SO_4$, followed by concentration under vacuum. The resulting residue was purified by diol column chromatography (chloroform), to obtain WA-016 (15.6 mg, 69%) as a colorless oily product.

WA-016: $^1$H NMR (500 MHz, $CDCl_3$) δ 4.58 (s, 2H), 4.64 (s, 2H), 7.17 (dd, J=7.5, 4.5 Hz, 1H), 7.19-7.23(m, 2H), 7.25 (bd, J=8.0 Hz, 1H), 7.62 (ddd, J=8.0, 7.5, 1.5 Hz, 1H), 7.66 (ddd, J=8.0, 7.5, 1.5 Hz, 1H), 8.48 (s, 1H), 8.51 (bd, J=4.0 Hz, 1H), 8.57 (bd, J=4.5 Hz, 1H).

$^{13}$C NMR (125 MHz, $CDCl_3$) δ 47.7, 53.0, 122.0, 122.5, 122.6, 122.8, 136.80, 136.83, 149.3, 149.9, 155.8, 156.2, 163.5.

The present invention is described above with emphasis on its preferred embodiments. It would be obvious for those skilled in the art that such embodiments may be modified, and equivalents of such embodiments may be used, as long as such modification and equivalents are within the idea of the present invention. The present description includes the contents described in the description and the drawings of JP 2014-002428 A, which is a basis of the priority of the present application. All publications, patents, and patent applications cited in the present description are hereby incorporated by reference.

The invention claimed is:

1. A method of treating malaria comprising administering a therapeutically effective amount of one or more compounds selected from the group consisting of
   (a) a compound of the Formula (III)

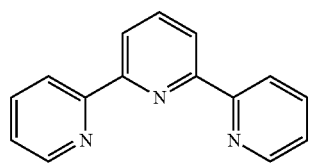

(III)

wherein
   each hydrogen (H) is optionally independently substituted with a halogen, $C_1$-$C_{10}$alkyl, $C_1$-$C_{10}$ alkoxy, phenyl, hydroxyl (—OH), carboxyl (—COOH), amino (—$NH_2$), benzamide (—$NHCOC_6H_5$), benzylamino (—$NHCH_2C_6H_5$), tert-butylamide (—NHCO-tBu), neopentylamino (—$NHCH_2$-tBu), —C(=O)OR, —S(=O)$_2$OR, or —OP(=O)(OR)(OR');
   R and R' each independently represent hydrogen or $C_1$-$C_{10}$ alkyl; and further,
   each hydrogen (H) in the alkyl, alkoxy, phenyl, "—$C_6H_5$" of the benzamide, "—$C_6H_5$" of the benzylamino, "-tBu" of the tert-butylamide, and "—$CH_2$—" and "-tBu" of the neopentylamino is optionally independently substituted with a halogen, hydroxyl, amino, —C(=O)OR, —S(=O)$_2$OR, or —OP(=O)(OR)(OR'), and
   (b) pharmaceutically acceptable salts and metal complexes thereof, to a subject suffering from malaria.

2. The method according to claim 1, wherein said compound represented by said Formula (III) is 2,2':6',2'''-terpyridine.

3. The method according to claim 1, wherein said metal complex is a zinc complex.

4. A method of treating malaria comprising administering a therapeutically effective amount of one or more compounds selected from the group consisting of
   (a) a compound of Formula (VIII)

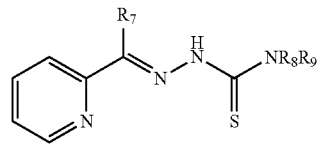

(VIII)

wherein, in Formula (VIII), $R_7$ represents Formula (II-1)

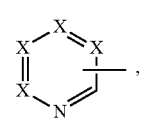

(II-1)

and
$R_8$ and $R_9$ are each independently $C_1$-$C_6$ alkyl or phenyl
   wherein, in Formula (II-1), any one of the Xs represents carbon (C) or nitrogen (N), and the other three Xs represent carbon (C), and
   wherein, in Formula (II-1) and Formula (VIII),
   each hydrogen (H) is optionally independently substituted with a halogen, $C_1$-$C_{10}$alkyl, $C_1$-$C_{10}$ alkoxy, phenyl, hydroxyl (—OH), carboxyl (—COOH), amino (—$NH_2$), benzamide (—$NHCOC_6H_5$), benzylamino (—$NHCH_2C_6H_5$), tert-butylamide (—NHCO-tBu), neopentylamino (—$NHCH_2$-tBu), —C(=O)OR, —S(=O)$_2$OR, or —OP(=O)(OR)(OR');
   R and R' each independently represent hydrogen or $C_1$-$C_{10}$ alkyl; and
   each hydrogen (H) in the alkyl, alkoxy, phenyl, "—$C_6H_5$" of the benzamide, "—$C_6H_5$" of the benzylamino, "-tBu" of the tert-butylamide, and "—$CH_2$—" and "-tBu" of the neopentylamino is optionally independently substituted with a halogen, hydroxyl, amino, —C(=O)OR, —S(=O)₂OR, or —OP(=O)(OR)(OR'), and (b) pharmaceutically acceptable salts and metal complexes thereof, to a subject suffering from malaria.

5. The method according to claim 4, wherein said compound represented by said Formula (VIII) is either

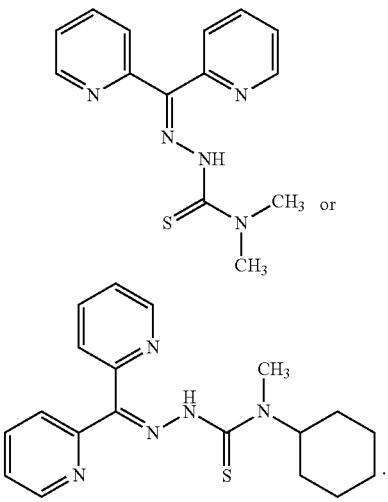

6. A method of treating malaria comprising administering a therapeutically effective amount of at least one zinc complex of a compound of Formula (VIII)

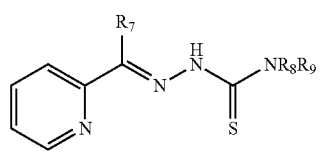

wherein, in Formula (VIII), R₇ represents Formula (II-1)

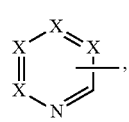

and

R₈ and R₉ are each independently hydrogen, C₁-C₆ alkyl, or phenyl, wherein in Formula (II-1), any one of the Xs represents carbon (C) or nitrogen (N), and the other three Xs represent carbon (C), wherein, in Formula (II-1) and Formula (VIII), each hydrogen (H) is optionally independently substituted with a halogen, C₁-C₁₀ alkyl, C₁-C₁₀ alkoxy, phenyl, hydroxyl (—OH), carboxyl (—COOH), amino (—NH₂), benzamide (—NHCOC₆H₅), benzylamino (—NHCH₂C₆H₅), tert-butylamide (—NHCO-Bu), neopentylamino (—NHCH₂-tBu), —C(=O)OR, —S(=O)₂OR, or —OP(=O)(OR)(OR');

R and R' each independently represent hydrogen or C₁-C₁₀ alkyl; and each hydrogen (H) in the alkyl, alkoxy, phenyl, "—C₆H₅" of the benzamide, "—C₆H₅" of the benzylamino, "-tBu" of the tert-butylamide, and "—CH₂—" and "-tBu" of the neopentylamino is optionally independently substituted with a halogen, hydroxyl, amino, —C(=O)OR, —S(=O)₂OR, or —OP(=O)(OR)(OR'), to a subject suffering from malaria.

7. A method of treating malaria comprising administering a therapeutically effective amount of at least one zinc complex of a compound of Formula (V)

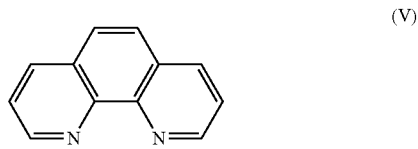

wherein each hydrogen (H) is optionally independently substituted with a halogen, C₁-C₁₀ alkyl, C₁-C₁₀ alkoxy, phenyl, hydroxyl (—OH), carboxyl (—COOH), amino (—NH₂), benzamide (—NHCOC₆H₅), benzylamino (—NHCH₂C₆H₅), tert-butylamide (—NHCO -tBu), neopentylamino (—NHCH₂-tBu), —C(=O)OR, —S(=O)₂OR, or —OP(=O)(OR)(OR');

R and R' each independently represent hydrogen or C₁-C₁₀ alkyl; and each hydrogen (H) in the alkyl, alkoxy, phenyl, "—C₆H₅" of the benzamide, "—C₆H₅" of the benzylamino, "-tBu" of the tert-butylamide, and "—CH₂—" and "-tBu" of the neopentylamino is optionally independently substituted with a halogen, hydroxyl, amino, —C(=O)OR, —S(=O)₂OR, or —OP(=O)(OR)(OR'), to a subject suffering from malaria.

8. The method according to claim 7, wherein said compound represented by said Formula (V) is either

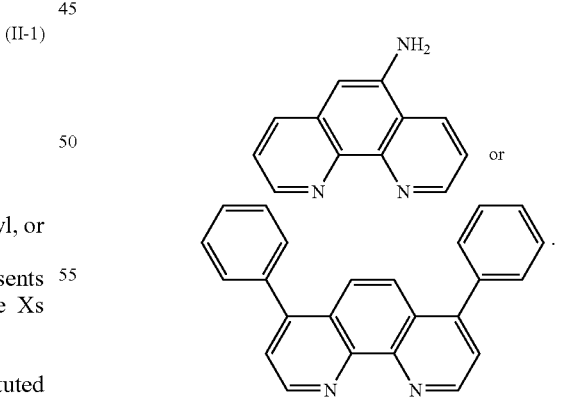

* * * * *

UNITED STATES PATENT AND TRADEMARK OFFICE
CERTIFICATE OF CORRECTION

PATENT NO.         : 10,137,119 B2
APPLICATION NO.    : 15/847432
DATED              : November 27, 2018
INVENTOR(S)        : Wada et al.

Page 1 of 1

It is certified that error appears in the above-identified patent and that said Letters Patent is hereby corrected as shown below:

In the Claims

Claim 2, Column 24, Lines 22-23, "Formula (III) is 2,2':6',2'''-terpyridine" should read "Formula (III) is 2,2':6',2''-terpyridine"

Signed and Sealed this
Eleventh Day of June, 2019

Andrei Iancu
*Director of the United States Patent and Trademark Office*